(12) United States Patent
Burke

(10) Patent No.: US 8,830,034 B2
(45) Date of Patent: Sep. 9, 2014

(54) SYSTEM AND METHOD TO DETERMINE STERILIZATION OF A DEVICE

(75) Inventor: Aaron Burke, Hamilton, MA (US)

(73) Assignee: EMD Millipore Corporation, Billerica, MA (US)

( * ) Notice: Subject to any disclaimer, the term of this patent is extended or adjusted under 35 U.S.C. 154(b) by 292 days.

(21) Appl. No.: 12/940,136

(22) Filed: Nov. 5, 2010

(65) Prior Publication Data

US 2011/0273272 A1 Nov. 10, 2011

Related U.S. Application Data

(60) Provisional application No. 61/261,539, filed on Nov. 16, 2009.

(51) Int. Cl.
| G08B 1/08 | (2006.01) |
| G08B 13/14 | (2006.01) |
| G06K 19/07 | (2006.01) |
| A61L 2/26 | (2006.01) |

(52) U.S. Cl.
CPC ........ G06K 19/0723 (2013.01); G06K 19/0717 (2013.01); A61L 2/26 (2013.01)
USPC ...................................... 340/10.1; 340/572.1

(58) Field of Classification Search
None
See application file for complete search history.

(56) References Cited

U.S. PATENT DOCUMENTS

| 4,862,088 | A | * | 8/1989 | Etienne et al. ................. 324/326 |
| 6,111,520 | A | * | 8/2000 | Allen et al. .............. 340/870.16 |
| 6,806,808 | B1 | * | 10/2004 | Watters et al. ............. 340/10.41 |
| 7,456,752 | B2 | | 11/2008 | Oberle |
| 2004/0061655 | A1 | | 4/2004 | Forster et al. |
| 2005/0012616 | A1 | | 1/2005 | Forster et al. |
| 2005/0017727 | A1 | | 1/2005 | Oberle |
| 2007/0176773 | A1 | | 8/2007 | Smolander et al. |
| 2007/0207579 | A1 | * | 9/2007 | Omura .......................... 438/253 |
| 2008/0012577 | A1 | | 1/2008 | Potyrailo et al. |
| 2008/0012579 | A1 | * | 1/2008 | Kuhns et al. .................. 324/652 |
| 2008/0036590 | A1 | * | 2/2008 | Gonzales et al. ........ 340/539.27 |
| 2009/0050814 | A1 | | 2/2009 | Seefeldt et al. |
| 2010/0079288 | A1 | | 4/2010 | Collins et al. |

FOREIGN PATENT DOCUMENTS

| CN | 1816818 A | | 8/2006 |
| JP | 2004-38391 A | | 2/2004 |
| JP | 2005-157485 A | | 6/2005 |
| JP | 2007-241651 A | | 9/2007 |
| SU | 1351825 A | * | 11/1987 |
| WO | 2010/087764 A1 | | 8/2010 |

OTHER PUBLICATIONS

Japanese Communication dispatched Oct. 2, 2012 in corresponding Japanese Patent Application No. 2010-256084.
Chinese Communication mailed Feb. 26, 2013 in corresponding Chinese patent application No. 201010610799.8.
European Communication mailed Mar. 11, 2013 in corresponding European patent application No. 10190720.2.

* cited by examiner

*Primary Examiner* — Brian Zimmerman
*Assistant Examiner* — Kevin Lau
(74) *Attorney, Agent, or Firm* — Nields, Lemack & Frame, LLC

(57) ABSTRACT

A system and method for verifying the occurrence of an environmental condition is disclosed. Rather than store information concerning the occurrence and/or success of the sterilization process, the present invention modifies the wireless transmission characteristics of the device. In some embodiments, the bandwidth of the wireless transceiver is altered as a result of undergoing sterilization. In other embodiments, the resonance frequency of the circuit is affected. In other embodiments, one or more of these parameters are affected based on other environmental conditions, such as shock or vibration.

9 Claims, 8 Drawing Sheets

SYSTEM AND METHOD TO DETERMINE STERILIZATION OF A DEVICE

This application claims priority of U.S. Provisional Application Ser. No. 61/261,539 filed Nov. 16, 2009, the disclosure of which is incorporated herein by reference.

BACKGROUND OF THE INVENTION

There are many applications in which it is desirable, or even imperative, to sterilize the objects being used. For example, the food industry requires that silverware, dishes, pots and other cooking utensils be sterilized. In addition, there is a requirement that pharmaceutical and medical devices also be sterilized. For example, scalpels and other medical instruments must all be sterilized prior to each use.

In other cases, there are single use applications, wherein the device to be sterilized is only used once before disposal. Items, such as needles used to draw blood, and syringes used for injections, must be sterilized prior to use. In addition to the medical field, there are similar requirements in the pharmaceutical industry. Filters, housings, and disposable components, such as bags, bioreactors and tubes, must be sterilized prior to use.

Sterilization can be performed in a number of ways. For example, sterilization using heat, such as autoclaving, is one common practice. In other embodiments, sterilization is performed by subjecting the object to radiation, such as gamma or beta radiation. Chemical reactions, such as those involving ethylene oxide, are another method used to sterilize a component. Often, the manufacturing process of these pharmaceutical components includes a sterilization step. Therefore, the manufacturer can guarantee customers that the selected component has undergone a sterilization procedure.

Recently, there has been a growing demand by pharmaceutical and medical device customers for independent verification that a device has been correctly processed during autoclaving, gamma sterilization, freezing, or shipping. Knowing that a device, such as a filter, bag, tube, or drug compound, has been processed correctly allows the customer to be more assured that the device can be used directly.

Typically, as described above, this assurance is provided with process engineering controls whereby a linear manufacturing sequence moves the device into and out of a process. However, there are various ways for the process to fail while still fulfilling the process controls. For instance, equipment performing the process, such as a gamma irradiator, may malfunction and not dose a filter correctly. Other devices may obscure the gamma rays, therefore reducing the dosage below the minimum level where bacteria may be killed.

Several attempts have been made to address this problem. For example, common to prepackaged medical devices, manufacturers use chemical color changing dyes to indicate a successful exposure to radiation.

Another method is a semiconductor component can be produced having minimal or limited protective coating on the substrate. In this case, gamma radiation penetrates the semiconductor package and affects the unprotected portion of the integrated circuit. The effect of the radiation may be to change a parameter of the circuit, such as threshold voltage or leakage current. The protected and unaffected portion of the component includes a sensing circuit that can determine any change in these parameters as a result of radiation. The user can then access this information, such as by using wireless or wired means.

However, this process requires that the operator understand the method and protocol for communication used by the device. For example, the operator must know what memory location within the device contains the information relevant to the radiation testing. In addition, this information may be stored in different locations and using different protocols, depending on the particular component and manufacturer.

Therefore, it would be beneficial if there were an independent method to confirm that a component had been properly sterilized which was simple to use and required no knowledge of the underlying circuitry. Such a method should determine whether the component was properly exposed to the elevated temperatures, depressed temperatures or radiation required to sterilize it. It would also be beneficial if there were a system that could be easily deployed and provide this confirmation without requiring the customer or user to perform difficult or cumbersome procedures.

SUMMARY OF THE INVENTION

The problems of the prior art are overcome by the system and method of the present invention. Rather than store information concerning the occurrence and/or success of the sterilization process, the present invention modifies the wireless transmission characteristics of the device. In some embodiments, the bandwidth of the wireless transceiver is altered as a result of undergoing sterilization. In other embodiments, the resonance frequency of the circuit is affected. In other embodiments, one or more of these parameters are affected based on other environmental conditions, such as shock or vibration.

DETAILED DESCRIPTION OF THE INVENTION

As described above, there is a need for quick, simple independent verification that a specific environmental condition has (or has not) occurred. Several examples of this include the need to verify that a medical or pharmaceutical device has been radiated, the need to verify that a particular drug has not been shaken, the need to verify that a device has been autoclaved. In some cases, devices exist which provide visual verification of these environmental conditions. For example, shipping dots that change color are used to monitor the temperature of an item in transit. Similarly, shock sensors exist which also provide visual confirmation that the item has or has not been subjected to excessive shock.

One common method to track assets and inventory is through the use of RFID tags. These tags are affixed to the item, and can be remotely interrogated by an RFID reader. The RFID tag itself includes a readable (and often rewritable) memory device, in which information about the part is stored. The information can include a description of the item, its date of manufacture, lot number, manufacturing process, expiration date, and other pertinent data.

The RFID tag also includes an antenna, tuned to operate at a particular frequency. In some embodiments, transmission occurs at 13.56 MHz, in others transmission is between 902 and 928 MHz, while in other embodiments, 2.4 GHz is used. Other frequency ranges are also possible and within the scope of the invention.

In the design of any RFID tag, there are often requirements to optimize the resonant frequency according to the RFID reader circuit. The radio frequency resonance is based on the fundamental equations for an LRC (inductor-resistor-capacitor) circuit. For an LRC circuit, the resonant frequency is defined as:

$$F_{res} = \frac{1}{2\Pi\sqrt{LC}}$$

where L is the inductance of the inductor in Henries and C is the capacitance in Farads.

Additionally, the bandwidth of the circuit is defined as:

$$\text{Bandwidth} = \frac{R}{2\Pi L}$$

where R is the resistance in Ohms and L is the inductance of the inductor in Henries.

Generally, the RFID microchip has certain electrical characteristics that require slight modification to tune it to the reader. The natural addition of the RF antenna to the RFID microchip will further change the overall tuning of the circuit. As is commonly done, an out-board circuit may be added to compensate for the changes and re-tune the circuit. Thus, the use of an external circuit is common in RFID tags.

In some embodiments, the out-board (or external) circuit contains a combination of passive components (such as inductors, capacitors, and resistors) to modify the overall bandwidth or resonance frequency of the RFID tag.

Figure 1:
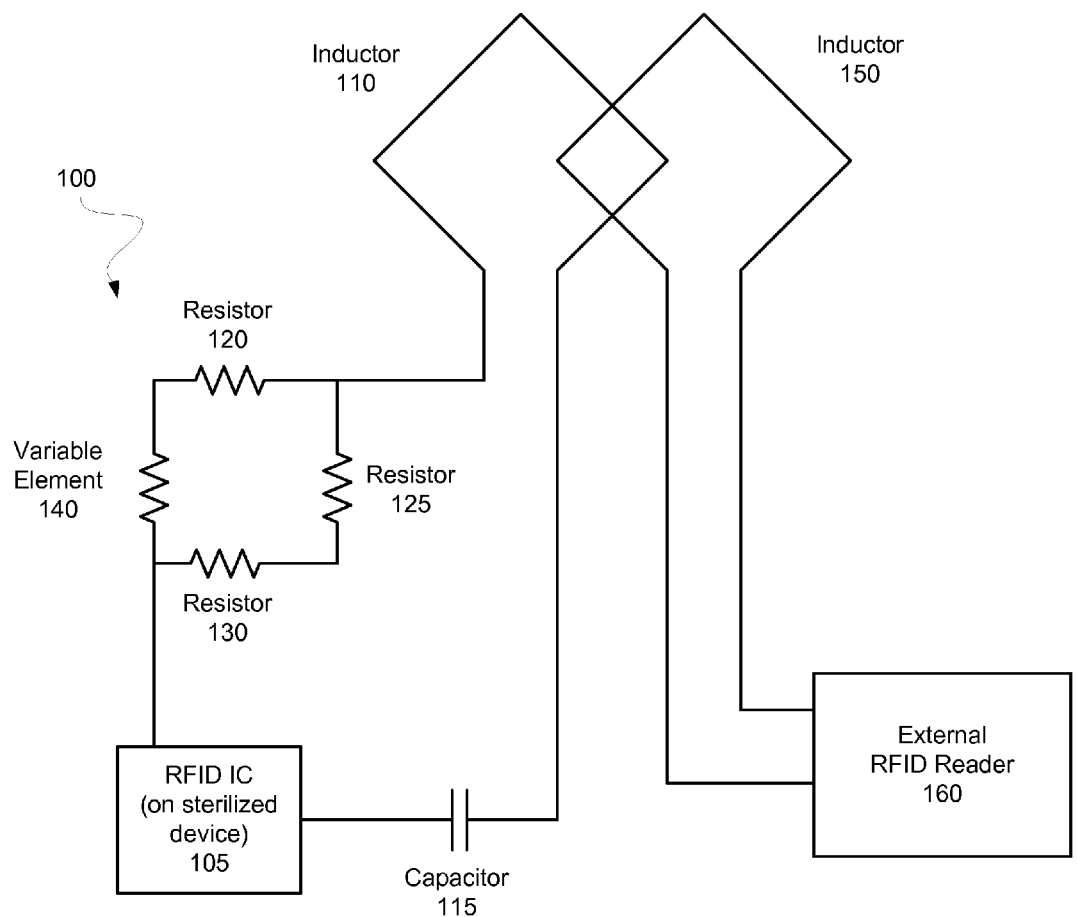
FIG. 1 is a first embodiment of the present invention.

In one embodiment, shown in FIG. 1, the out-board circuit 100 is a combination of resistors 120, 125, 130 in a Wheatstone bridge configuration where one component 140 is chosen to intentionally change its value based on the quality and kind of environmental condition. In other words, when a particular environmental condition, such as shock, elevated temperature or radiation, occurs, the variable component's initial or default value will be altered. In the case of a resistor, this change will affect the bandwidth of the tag without affecting its resonant frequency. The RFID chip 105 is in electrical communication with a capacitor 115 and an inductor 110, which are arranged in series. In other embodiments, these two components can be arranged in parallel. The LC circuit is also in series with the Wheatstone configuration. This Wheatstone configuration has two possible equivalent resistances, based on the value of variable component 140.

Figure 2A:
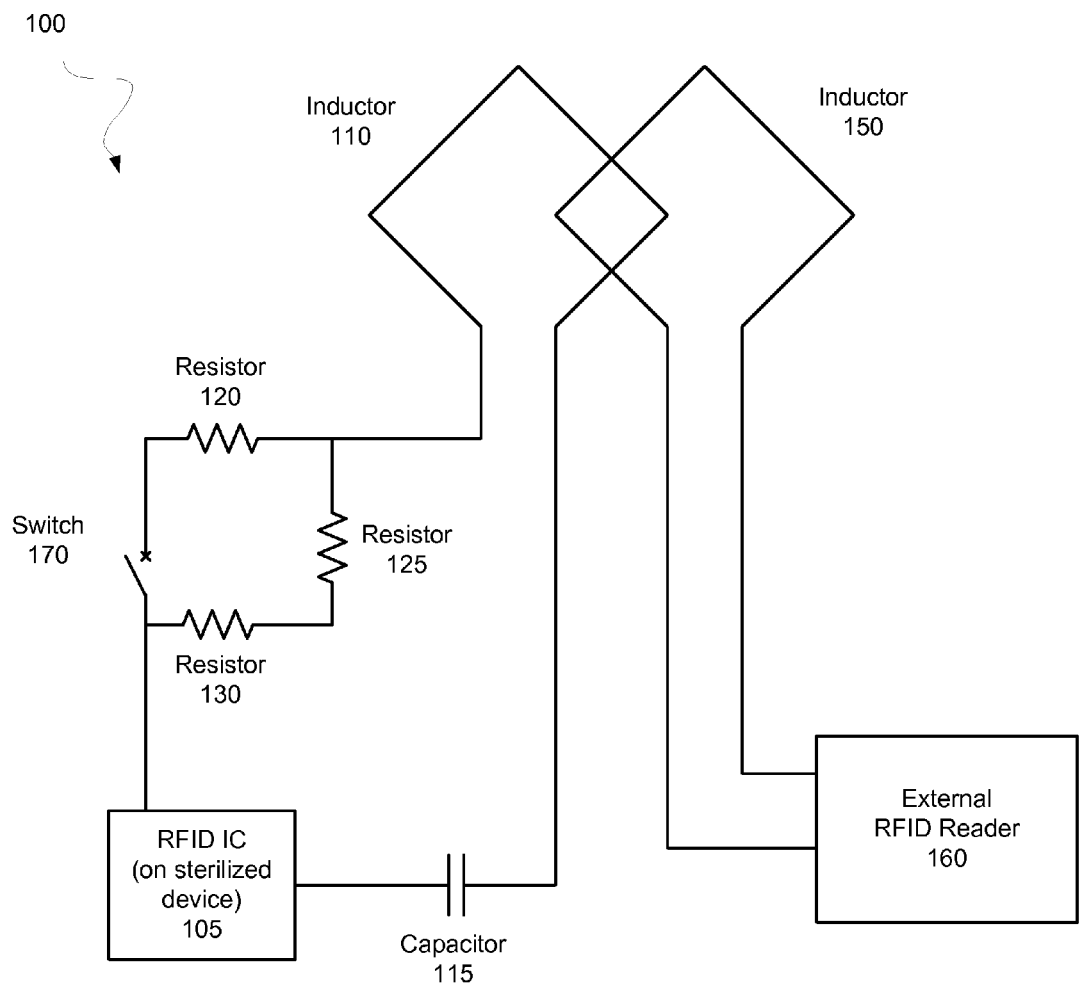
FIG. 2a is a second embodiment of the present invention.

In a second embodiment, shown in FIG. 2a, a switch 170 is placed in series with one of the resistors 120 such that the particular environmental condition opens the switch 170. The switch has two states, closed whereby the branch of the circuit in series with the switch (i.e. Resistor 120) is connected to the circuit, and open, whereby the series branch is disabled. Thus, when the switch 170 is closed, the overall resistance is lower since a resistor 120 in parallel with resistors 125, 130 causes the resulting equivalent resistance to be lower than that of the resistor 125, 130 alone. Thus, the bandwidth of the circuit increases when the switch 170 is open, as the resistance is higher in that state.

The switch could be chosen from a variety of components such as a thermal switch for analyzing an autoclave cycle or a simple classic transistor diode for analyzing radiation sterilization. Again, this configuration affects the bandwidth of the circuit, without impacting its resonance frequency.

Figure 2B:
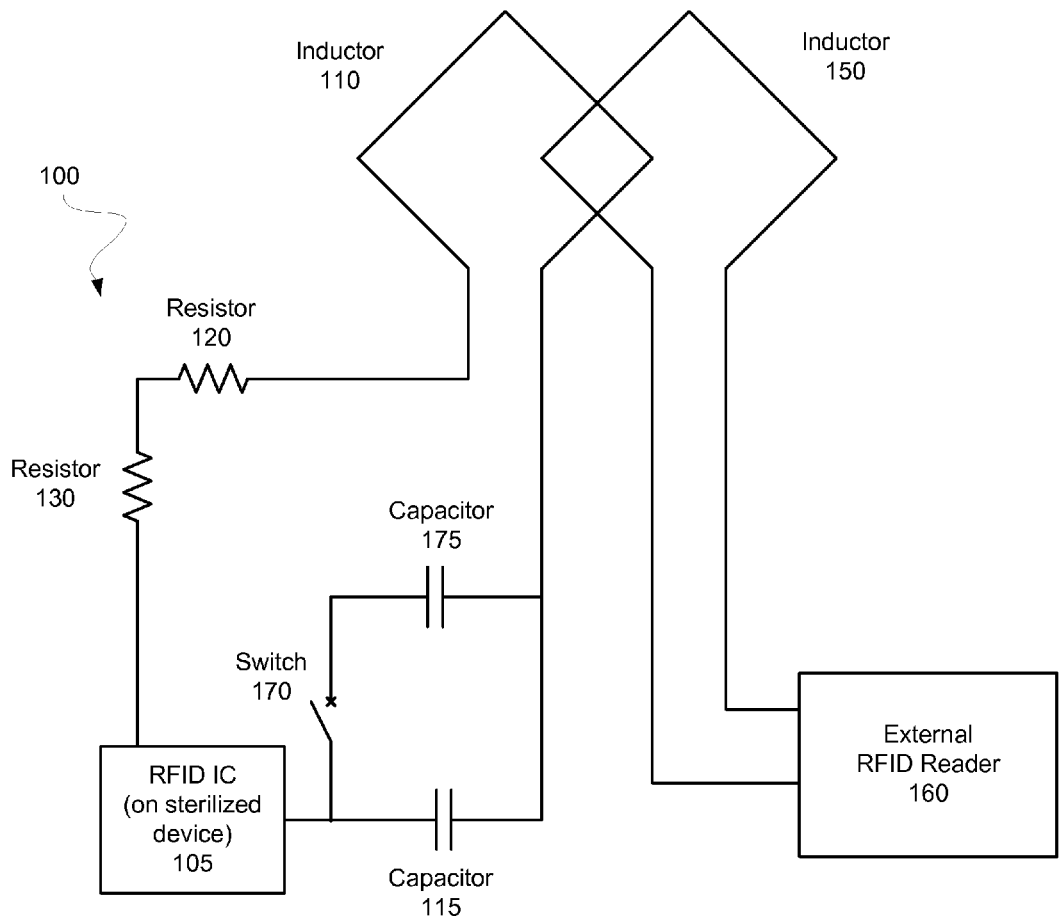
FIG. 2b is a third embodiment of the present invention.

In a third embodiment, shown in FIG. 2b, a switch 170 or other variable component is inserted in series with a second capacitor 175. In this embodiment, the state of the variable element 170 will affect the equivalent capacitance of the circuit. In this case, when the switch is closed, the capacitance will be increased, and will be reduced when the switch is open. This configuration affects the resonant frequency, but not the bandwidth.

Of course, other configurations are possible and within the scope of the invention. In some embodiments, an external tunable LRC circuit is employed. A variable component capable of two different states is used in this external circuit. The component changes from its default state to its altered state based on an environmental condition of interest, such as shock, temperature or radiation.

In other embodiments, the external tunable circuit may consist of only some portions of the LRC circuit. For example, certain elements of the circuit may be integrated into the RFID integrated circuit (such as the capacitor or inductor. In these embodiments, one or more external components may be used to affect the wireless parameters of the device and may include an inductor, capacitor, resistor or any combination thereof. The same techniques described above can be used to vary the behavior of this external circuitry.

Shock can change the electrical state of a variety of devices, such as a physical impact switch. Such a switch is constructed using a fine gauge filament suspended within a mounting device. An impact in a direction orthogonal to the filament would cause it to loosen from the suspension points. These like this function similar to common light bulbs or fuse which are susceptible to impact. Different levels of shock can be detected by varying the thickness of the filament and the robustness of its connection to the suspension points.

Temperature variations can cause irreversible changes to devices, such as certain resistors or thermal fuses. Resistors made of oxidizable components, such as carbon, will oxidize with increases in temperature irreversibly. Other resistors that are constructed of non-oxidizable materials, such as metal oxides, or packed to be impervious to the environmental changes remain stable and do not change value.

Sufficiently energetic radiation causes changes to devices such as resistors and semiconductor junctions. Radiation causes change the resistance value of a resistor by further oxidizing the base material or modifying the crystalline or polymer structure. Semiconductor junctions, such as n-p or p-n type diodes, are affected by radiation due to changes in the crystalline structure and the dislodging of dopant material within the conductance band.

Figure 2C:
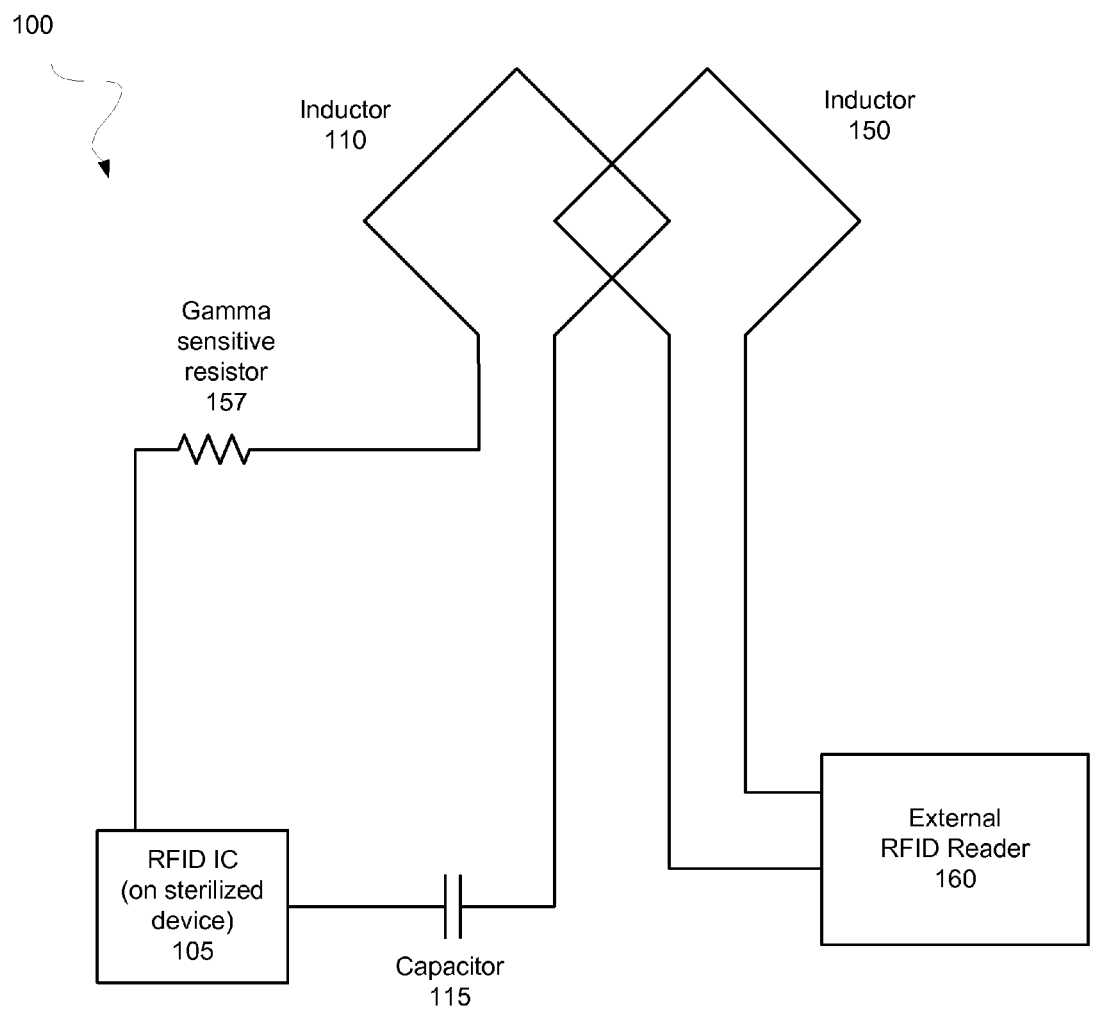
FIG. 2c is another embodiment of the present invention.

The variable component may be one such that its state is irreversibly altered by the environmental condition of interest. Therefore, the effect can be measured after the condition has passed. It is advantageous to choose a circuit design that will change in a predictable way in response to the condition while still retaining a general operability where the bandwidth or resonant frequency can be measured. In some embodiments, a component that changes its default value but does not become entirely inoperable can be used in a simple LRC circuit. FIG. 2c shows a simple RLC circuit where the value of the gamma sensitive resistor 157 varies relative to its exposure to gamma radiation. In this scenario, the bandwidth of the circuit varies as a function of the exposed level of radiation. However, for a component that changes catastrophically, such as a thermal fuse, a Wheatstone bridge or any parallel arrangement can be used. In either case, the other supporting components should preferably be chosen to be resilient to the environmental condition.

In other embodiments, components that reversibly or predictably change their conditions can be used. Such components include resistors or capacitors that meet military, radiation-hard, or high performance standards, such as from Presidio Components, Inc.

Figure 3:
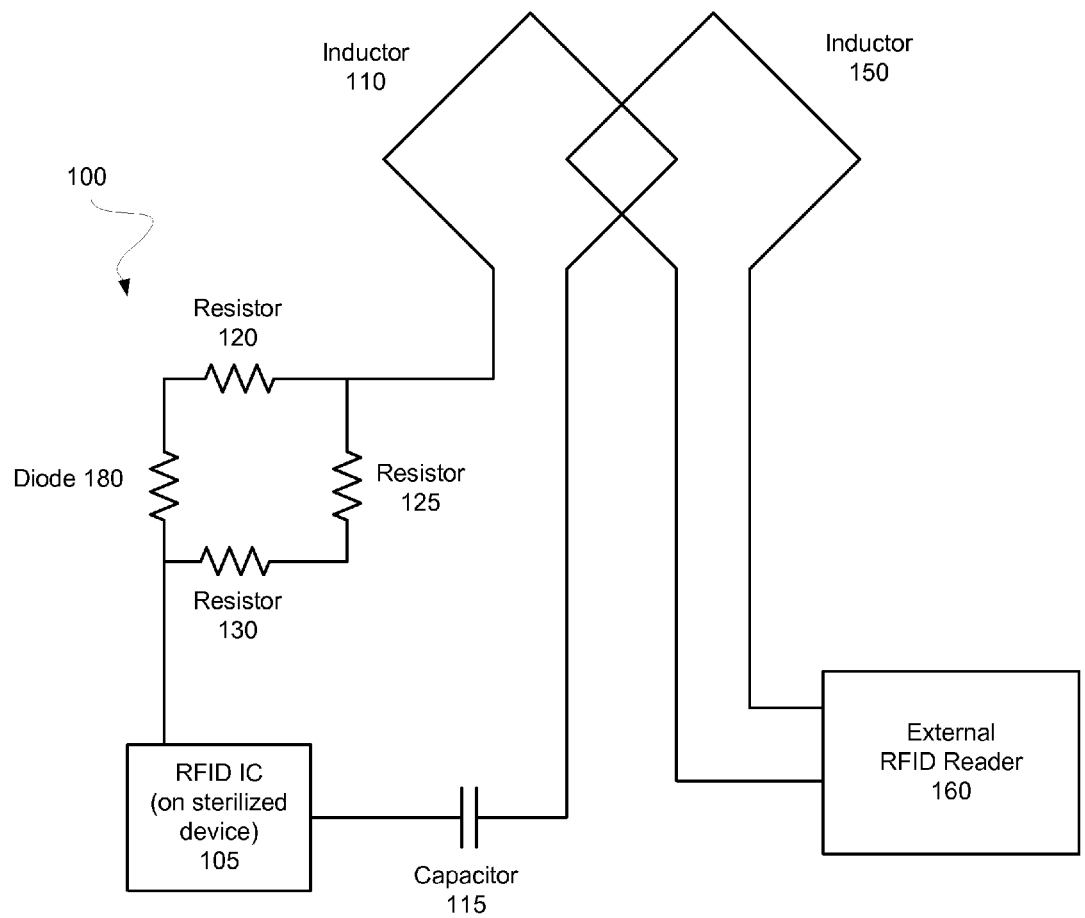
FIG. 3 is another embodiment of the present invention.

Another embodiment is shown in FIG. 3. In this embodiment, there are parallel resistor branches, where one of these branches contains a resistor 120 and one or more diodes 180. The other branch includes one or more resistors, such as resistors 125, 130. In normal operation, no current flows through the path with the diodes, as one of the diodes is always reverse biased. However, the exposure of gamma radiation often affects one or more characteristics of a diode, such as its forward bias voltage, its reverse bias voltage, or its leakage current, thereby allowing current flow. Thus, the diodes will begin to conduct, allowing the second resistor branch to affect the equivalent resistance of the circuit. This change in resistance causes a corresponding change in bandwidth, which can be remotely detected.

As stated above, other environmental conditions can be detected using the present invention. For example, to detect temperature, devices can be fabricated which irreversibly change as a result of exposure to low temperature. Generally, standard electrical components do not change irreversibly at depressed temperatures, such as −80° C. However, such devices could be constructed that irreversibly physically contract or dissipate a resistive material that will cause such a desired change in its electrical value. Other low temperature devices can be constructed similar to a thermal fuse, whereby the joint between the two conductors contracts beyond the elastic point and separates thereby opening the circuit. Such components can be used in configurations, such as those shown in FIGS. 2a and 2b. The description of such an irreversible low temperature device does not limit the embodiments to this device as others are included in this invention.

The measurement of shock can be accomplished by using one or more resistor shock fuses arranged in a parallel configuration. In the case of a single fuse, the device can only detect whether the device has been subjected to shock over a certain threshold. The use of two fuses, having different shock thresholds allows the detection of 3 levels (low, where neither fuse breaks, medium where one fuse breaks and high where both fuses break). The use of more shock fuses obviously allows greater granularity if required. A shock fuse can be constructed by a resistive member suspended across an opening where the end connection breaks according to correlated impacts. A lightbulb filament represents one such embodiment. Alternatively, an accelerometer component represents a solid-state embodiment. Such components can be used in various configurations, such as that shown in FIGS. 2a and 2b.

Figure 4A:
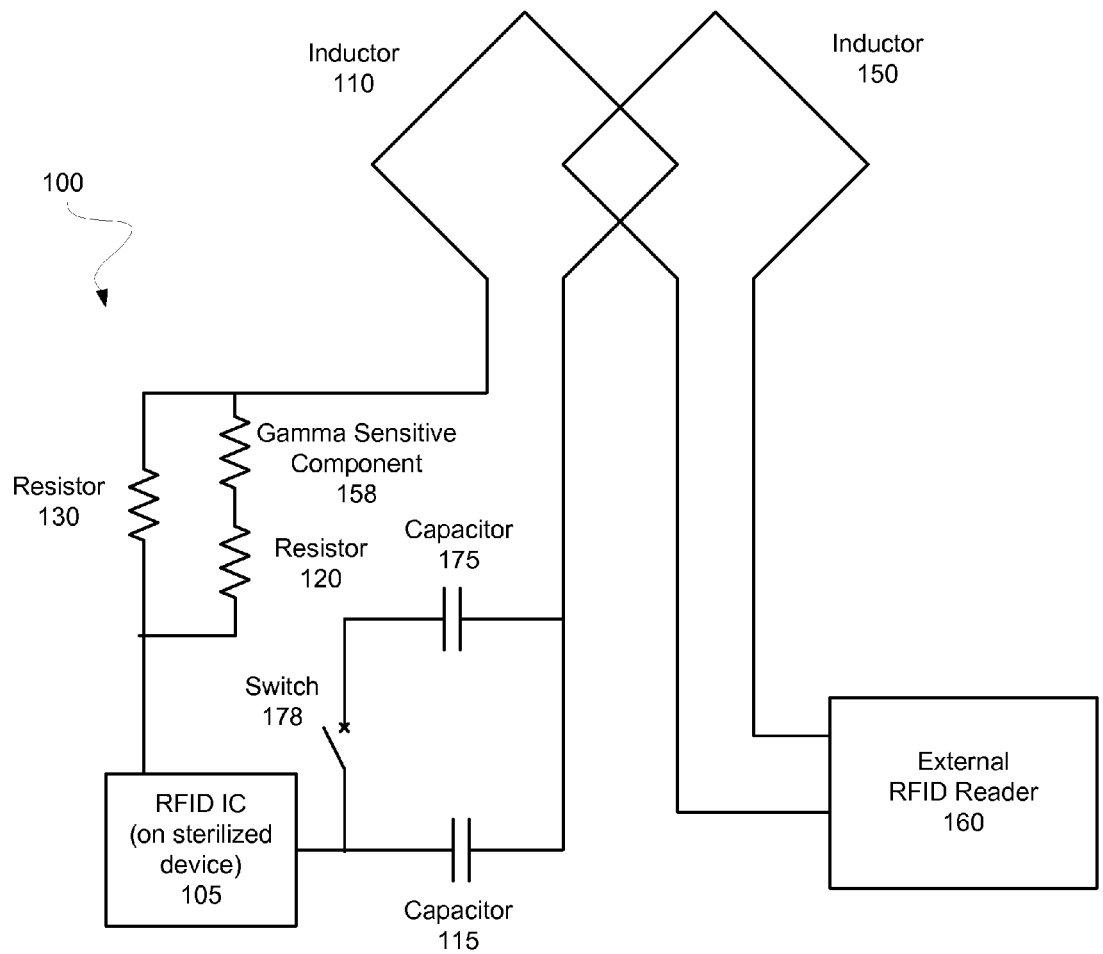
FIGS. 4a and 4b are embodiments to detect two different environmental condition.

In some embodiments, this invention can be used to measure two independent environmental conditions. For example, a gamma radiation sensitive component 158 can be introduced to the circuit, as shown in FIG. 4a. Such a configuration creates a change in bandwidth. A second variable component 178, such as one sensitive to depressed temperature, can be introduced in the circuit, shown as is shown in FIG. 4a. This component 178 would affect the resonant frequency of the circuit. Thus, two different environmental conditions can be independently determined using this invention.

Figure 4B:
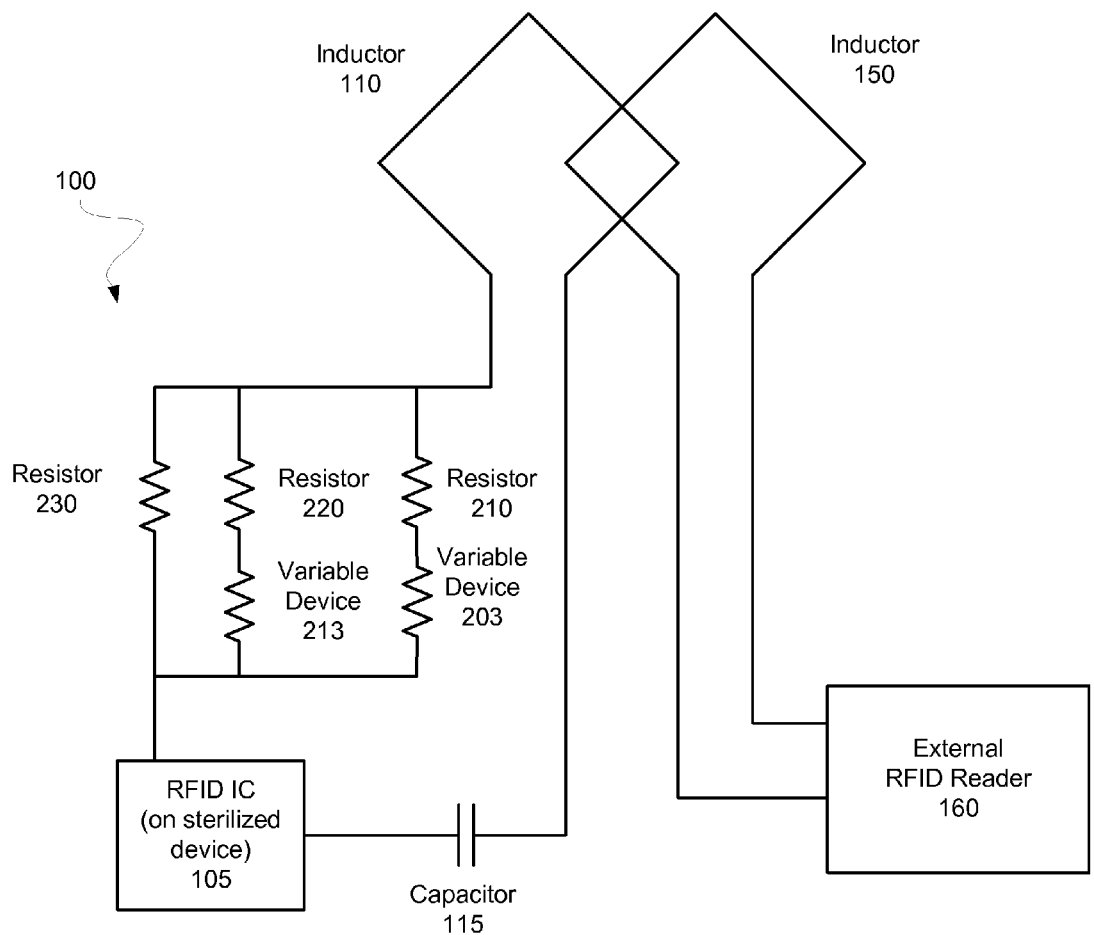

In some embodiments, as shown in FIG. 4b, the two independent environmental conditions can be detected by varying only a single parameter. For example, suppose three parallel resistor branches are used, where each branch has a different series resistance. The first branch includes a series variable device 203, such as a gamma sensitive device, and a first resistor 210, having a first resistance. The second branch includes a second variable component 213, such as one sensitive to depressed temperature, and a second resistor 220, having a second resistance. The third branch is impervious to environmental conditions and therefore has a constant resistance 230. If no environmental conditions are observed, the equivalent resistance of this circuit will be based on the three resistance values 210, 220, 230. If gamma radiation occurs, the resistance of this circuit will be based on the second resistance value 220 and third resistance value 230. If depressed temperatures occur, the resistance of the circuit will be based on the first resistance value 210 and third resistance value 230. If both gamma and depressed temperatures occur, the resistance of the circuit will be equal to the third resistance value 230.

Figure 5:
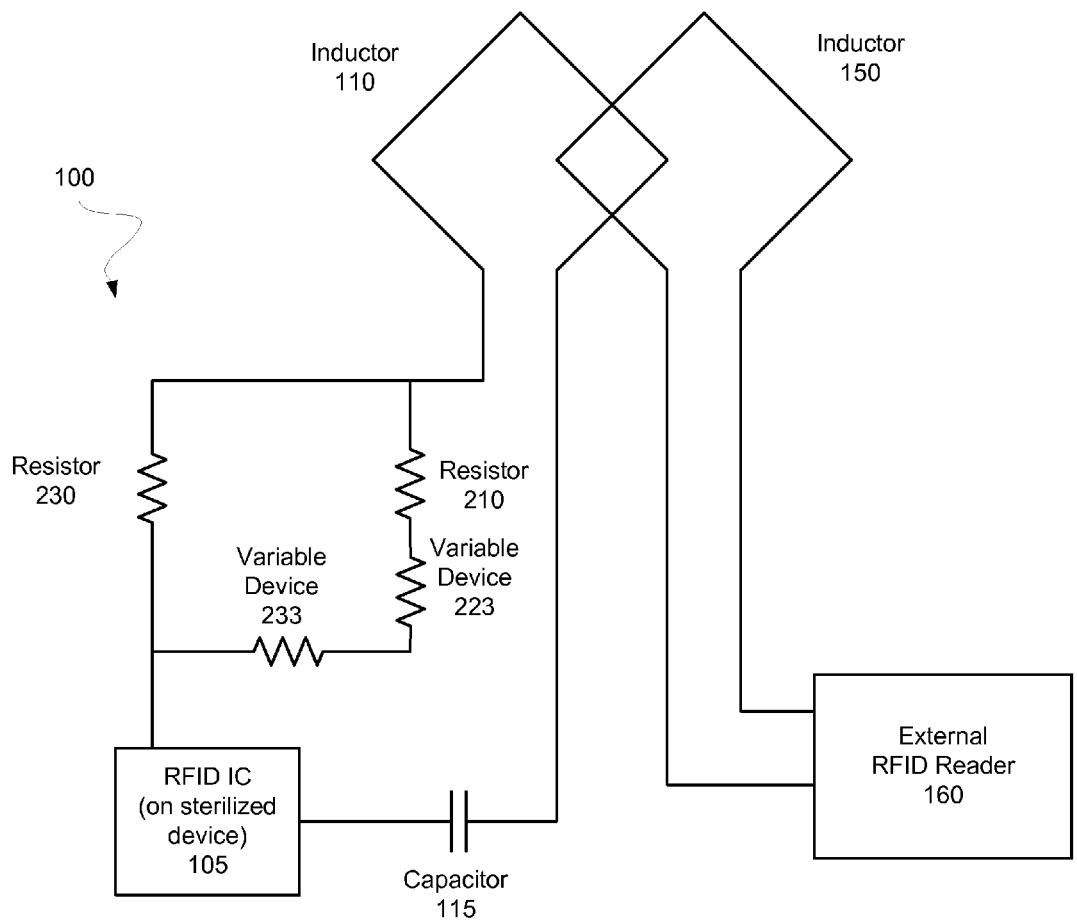
FIG. 5 is another embodiment of the present invention.

In another embodiment, it may be important to know whether sterilization, such as by autoclaving or gamma radiation, has been performed, but not important to know which process was used. In this scenario, as shown in FIG. 5, two variable components 223, 233, each sensitive to at least one of the environmental conditions, can be placed in series, such that the failure or alteration of either affects the circuit. In one embodiment, the components can be placed in series with resistor 210, and these components are in parallel with resistor 230. Thus, the occurrence of either condition removes resistor 210 from the circuit, and the equivalent resistance is simply the resistance of resistor 230.

Analysis of the tag to determine if it has experienced the condition can include determining changes in frequency, bandwidth, or read distance. However, any of these may be modified by the electrical interference in the environment during the analysis. The analysis is further complicated by variations between the original reference reader circuit and the on-site circuit. Some or all of these variations can be accommodated by recording specific setup and measurement values on the RFID tag to be read by the on-site reader. In some embodiments, the changes to the variable component serve to improve the parameters of the circuit, whereas the pre-condition of the component will not be optimally tuned. This technique allows the analysis to be conclusive and correlated to the condition and not be confounded with other changes to the circuit.

Furthermore, it is highly desirable that the other components in the overall circuit, such as the remaining capacitors, inductors and resistors, be insensitive to the environmental condition of interest. In addition, the RFID integrated circuit 105 used should also preferably be able to withstand the environmental condition, whether elevated or depressed temperatures, shock or radiation. In the case of radiation, the RFID integrated circuit 105 can be produced based on a non-change based storage technology, such as FRAM or MRAM. Alternatively, a process that is highly insensitive to radiation, such as Silicon on Insulator (SOI) can be employed to produce the RFID integrated circuit 105.

Various means can be imagined to accomplish the protection of the remaining insensitive components can be made this way including shielding from the heat, radiation, and shock. For instance, a heat sensitive component can be thermally insulated by the use of foam, vacuum or mechanical isolation. Radiation sensitive components can be shielded by the use of dense materials, such as lead, or by perpendicular orientation thereby reducing the incident radiation. Shock sensitive components can be isolated from the impact by use of absorptive materials, such as foam or springs.

What is claimed is:

1. A wireless identification device, comprising: an RFID integrated circuit, and an external circuit, adapted to tune the frequency of wireless transmissions, said external circuit comprising an inductor, a capacitor, a resistor, a first variable component, wherein said first variable component has an open state and a closed state, wherein said state of said first variable component is determined based upon exposure to a first environmental condition, and a second variable component, wherein said second variable component has an open state and a closed state, wherein said state of said second variable component is determined based upon exposure to a second environmental condition, said second environmental condition is of a kind different than said first environmental condition, and wherein said inductor, said capacitor, said resistor, said first variable component and said second variable component determine a resonant frequency and bandwidth of said device, wherein said first variable component affects only said bandwidth and said second variable component only affects said bandwidth.

2. The wireless identification device of claim 1, wherein said first variable component is in series with said resistor and said external circuit comprises a second resistor in series with said second variable component, wherein said second resistor and said second variable component are in parallel with said first variable component and said resistor.

3. The wireless identification device of claim 1, wherein said first environmental condition and said second environmental condition are selected from the group consisting of shock, elevated temperature, depressed temperature and radiation.

4. A method of verification that an item has been subjected to at least one of a plurality of environmental conditions, comprising: affixing an RFID device on said item, said RFID device comprising an RFID integrated circuit, and an external circuit, adapted to tune the frequency of wireless transmissions, said external circuit comprising an inductor, a capacitor, a resistor, a first variable component, wherein said first variable component has an open state and a closed state, wherein said state of said first variable component is determined based upon exposure to a first of said plurality of environmental conditions and a second variable component, wherein said second variable component has an open state and a closed state, wherein said state of said second variable component is determined based upon exposure to a second of said plurality of environmental conditions, said second environmental condition is of a kind different than said first environmental condition, and wherein said inductor, said capacitor, said resistor, said first variable component and said second variable component determine a resonant frequency and bandwidth of said device, wherein said first variable component affects only said bandwidth and said second variable component only affects said bandwidth; interrogating said RFID device with an external RFID reader; comparing said bandwidth to a predetermined value; and verifying said item has been subjected to at least one of said plurality of said environmental conditions based on the result of said comparison.

5. The method of claim 4, wherein said first and said second of said plurality of environmental conditions are selected from the group consisting of shock, elevated temperature, depressed temperature and radiation.

6. The method of claim 4, wherein said first variable component is in series with said resistor and said external circuit comprises a second resistor in series with said second variable component, wherein said second resistor and said second variable component are in parallel with said first variable component and said resistor.

7. The wireless identification device of claim 1, wherein said first variable component is in series with said resistor, said second variable component is in series with a second resistor, and said external circuit comprises a third resistor, in parallel with said first variable component and said resistor and in parallel with said second variable component and said second resistor.

8. The method of claim 4, wherein said first variable component is in series with said resistor, said second variable component is in series with a second resistor, and said external circuit comprises a third resistor, in parallel with said first variable component and said resistor and in parallel with said second variable component and said second resistor.

9. The method of claim 4, further comprising determining which of said first and second environmental conditions said device has been exposed to.

* * * * *